United States Patent [19]

Müller et al.

[11] Patent Number: 4,520,673
[45] Date of Patent: Jun. 4, 1985

[54] INSPECTION DEVICE, ESPECIALLY FOR STEAM GENERATOR TUBES

[75] Inventors: Thomas Müller, Erlangen; Rainer Bauer, Herzogenaurach, both of Fed. Rep. of Germany

[73] Assignee: Kraftwerk Union Aktiengesellschaft, Mülheim, Fed. Rep. of Germany

[21] Appl. No.: 462,052

[22] Filed: Jan. 28, 1983

[30] Foreign Application Priority Data

Jan. 29, 1982 [DE] Fed. Rep. of Germany ....... 3202883

[51] Int. Cl.³ .............................................. G01N 29/04
[52] U.S. Cl. ........................................ 73/623; 226/76
[58] Field of Search .................... 73/623, 638, 432 A; 414/751; 226/76, 86, 85

[56] References Cited

U.S. PATENT DOCUMENTS

| | | | |
|---|---|---|---|
| 3,066,548 | 12/1962 | Shapiro | 226/76 |
| 3,699,688 | 10/1972 | Estes | 414/751 |
| 3,926,040 | 12/1975 | Cowell | 73/623 |
| 3,934,731 | 1/1976 | Muller et al. | 414/749 |

Primary Examiner—Anthony V. Ciarlante
Attorney, Agent, or Firm—Herbert L. Lerner; Laurence A. Greenberg

[57] ABSTRACT

Inspection device, including a probe having a thrust hose for moving the probe, the thrust hose having mutually equidistant holes formed therein along a generatrix line thereof, a feed device having drive wheels for engaging the thrust hose to move the probe, and plugs disposed on at least one of the drive wheels for insertion in the holes.

6 Claims, 2 Drawing Figures

INSPECTION DEVICE, ESPECIALLY FOR STEAM GENERATOR TUBES

The invention relates to an inspection device, especially for steam generator tubes, with a probe which is moved by means of a thrust hose and by a feed device gripping the thrust hose with drive wheels.

In a device of the above-mentioned type which is known from German Patent DE-PS No. 22 64 143 corresponding to U.S. Pat. No. 3,934,731, the drive wheels of the feeding device grip the thrust hose through friction. However, the feeding force which can be supplied in this way is not very large because there are limits to the pressure in view of the desired flexibility of the thrust hose. Therefore, difficulties can arise if the probe threatens to become stuck in curves or at incrustations.

It is accordingly an object of the invention to provide an inspection device, especially for steam generator tubes, which overcomes the hereinafore-mentioned disadvantages of the heretofore-known devices of this general type.

With the foregoing and other objects in view there is provided, in accordance with the invention, an inspection device, comprising a probe having a thrust hose for moving the probe, the thrust hose having mutually equidistant holes formed therein along a generatrix line thereof, a feed device having drive wheels for engaging the thrust hose to move the probe, and plugs disposed on at least one of the drive wheels for insertion in the holes. In this way, a positive contact is obtained which allows the transmission of larger forces. In this manner, a secure movement of probes for ultrasonic measurements can also be achieved, which furthermore has a seal increasing the friction in order to hold the medium required for coupling in the steam generator tubes by means of the seal.

In accordance with another feature of the invention, the plugs have pointed ends. This is done in order to facilitate engagement with the holes. The term "pointed" also includes structures in which the free ends of the plugs each become a round dome.

In accordance with a further feature of the invention, the holes and plugs have circular cross sections, although in principle the invention can also be realized with other cross sections. Through the use of circular cross sections, however, a particularly low stress on the hose, which commonly is made of plastic, is obtained, so that wear remains small.

The wear is particularly small if there is some difference between the diameter of the hole and the diameter of the plugs leaving a clearance, because the plugs then become active only if the feed hose or the probe are jammed, while the normal motion is provided by friction.

In accordance with an added feature of the invention, the thrust hose has a diameter having a given dimension, and the holes are spread apart from each other by a distance being at least substantially as large as the given dimension, "substantially" meaning a deviation of about 15% more or less. Any pitch in this range has exhibited good results in tests.

In accordance with an additional feature of the invention, the holes each have a diameter being between one-third and one-tenth of the distance between the holes, because then the engagement of the plugs takes place without difficulty with the commonly used dimensions of the drive wheels. In view of the forces to be transmitted, in accordance with again another feature of the invention, the thrust hose has a wall having a given thickness, and the holes each have a diameter being between 0.5 and 2.5 times the given thickness.

In accordance with a concomitant feature of the invention, the feed device includes two drive wheels having the support plugs disposed thereon, the support plugs on one of the drive wheels being offset relative to the support plugs on the other of the drive wheels. Preferably, it is in the range of the plug diameter.

Other features which are considered as characteristic for the invention are set forth in the appended claims.

Although the invention is illustrated and described herein as embodied in an inspection device, especially for steam generator tubes, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompaying drawings, in which.

Figure 1:
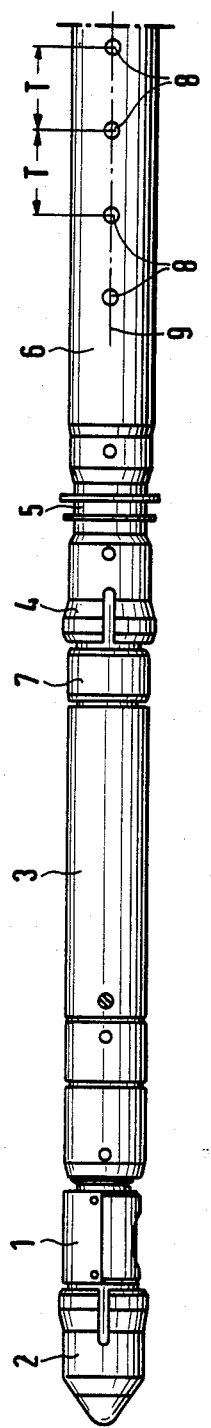
FIG. 1 is a diagrammatic side-elevational view of the probe as a whole.

Referring now to the figures of the drawing and first particularly to FIG. 1 thereof, it is seen that the ultrasonic probe which serves for determining material discontinuities, has an essential part being a rotatable testing head 1, which is supported rotatably in a guide tip 2, and a central part 3. The central part 3 is followed by a further guide part 4 with a sealing body 5 to which a thrust hose 6 is fastened. Between the guide part 4 and the central part 3, a plug connection 7 with a bayonet lock is provided.

The thrust hose 6 is a plastic hose of circular cross section with an outside diameter of 18 mm and a wall thickness of 1.5 mm and is formed, for instance, of polyethelene. The thrust hose 6 has a perforation with circular holes 8 which have a diameter of 3.5 mm and are disposed with a spacing or pitch T of 18 mm along a generatrix 9.

Figure 2:
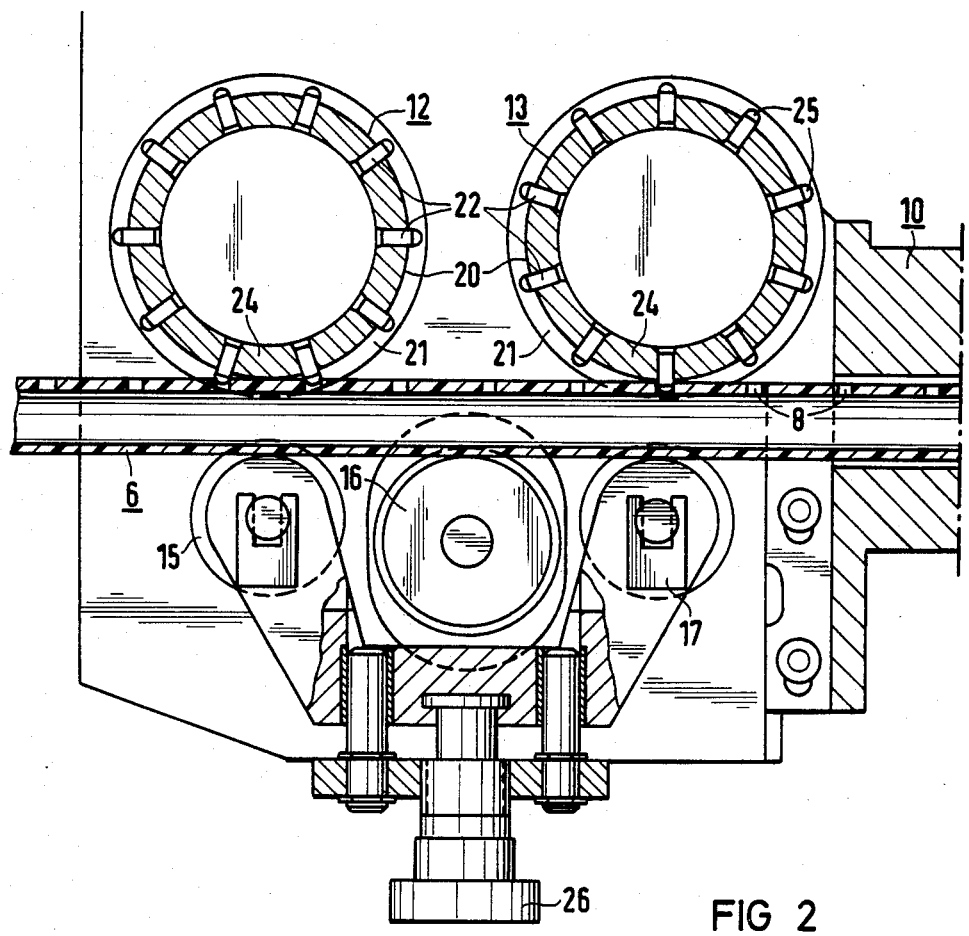
FIG. 2 is a partially cross-sectional fragmentary view, rotated through 90°, of the feed device essential for the invention.

For testing tubes of a steam generator in a nuclear power station, preferably with a pressurized-water reactor, which are not shown in detail, the thrust hose 6 is put in motion by a feed device 10 shown in FIG. 2. To this end, the thrust hose 6 is guided between two identical drive wheels 12, 13 and three pressure wheels 15, 16 and 17 which are disposed symmetrically opposite the drive wheels.

The drive wheels 12, 13 are set in motion by a non-illustrated electric motor. The drive wheels transport the thrust hose 6 in normal operation by frictional engagement with a cylindrical surface 20 at which the thrust hose is guided laterally by means of rims or rubbing strips 21. In the case of larger thrust forces, plugs 22 then become effective and engage the holes 8 of the thrust hose 6.

The cylindrical plugs 22 each have a 2.8 mm diameter and are inserted from the inside into the hollow cylinders 24 of the drive wheels 12, 13. The free end of the plugs 22 protrude with hemispherical tips 25 at a distance of 3 mm from the surface 20. This corresponds practically to the size of the diameter which is 2.8 mm and thus is far larger than the wall thickness of the thrust hose 6, to such an extent that the thrust hose 6 is in contact with the cylindrical part of the plugs 22.

In each drive wheel 12, 13, ten plugs 22 are disposed in such a way as to be uniformly distributed. However, the pitch of the plugs is circumferentially offset in the two drive wheels by one half the pitch angle, i.e. by 18°, as is clearly shown in FIG. 2. Therefore, at least one plug 22 is always in sufficient engagement with the thrust hose 6.

The pressure wheels 15, 16, 17 which, if required, can also be driven, have a curvature adapted to the circumference of the thrust hose 6. The distance between the pressure wheels and the drive wheels 12, 13 can be set by means of a handwheel 26, especially in order to facilitate the insertion of the thrust hose 6. In addition, the pressure wheels 15 and 17 are resiliently supported transversely to the thrust hose.

The construction of the thrust hose 6 just described for the testing of steam generator tubes can also be used for inspection devices for other heat exchangers which are to be tested by remote control because of chemical aggressiveness or toxicity or elevated temperature. Eddy current probes, endoscopes and similar devices can further be considered as inspection devices.

The foregoing is a description corresponding to German Application No. P 32 02 883.0, dated Jan. 29, 1982, the International priority of which is being claimed for the instant application, and which is hereby made part of this application. Any discrepancies between the foregoing specification and the aforementioned corresponding German application are to be resolved in favor of the latter.

We claim:

1. Inspection device, comprising a probe having a flexible thrust hose for moving said probe, said thrust hose having mutually equidistant holes formed therein along a generatrix line thereof, a feed device having two drive wheels for engaging said thrust hose to move said probe, and plugs disposed on said drive wheels for insertion in said holes, said support plugs on one of said drive wheels being circumferentially offset relative to said support plugs on the other of said drive wheels.

2. Inspection device according to claim 1, wherein said plugs have pointed ends.

3. Inspection device according to claim 1, wherein said holes and plugs have circular cross sections.

4. Inspection device according to claim 1, wherein said thrust hose has a diameter having a given dimension, and said holes are spaced apart from each other by a distance being at least substantially as large as said given dimension.

5. Inspection device according to claim 3, wherein said holes each have a diameter being between one-third and one-tenth of the distance between said holes.

6. Inspection device according to claim 3, wherein said thrust hose has a wall having a given thickness, and said holes each have a diameter being between 0.5 and 2.5 times said given thickness.

* * * * *